United States Patent [19]

Hope

[11] Plant 4,745

[45] Jun. 16, 1981

[54] KALANCHOE NAMED YUCATAN

[75] Inventor: Claude Hope, Cartago, Costa Rica

[73] Assignee: Pan-American Plant Company, West Chicago, Ill.

[21] Appl. No.: 150,591

[22] Filed: May 16, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new kalanchoe cultivar developed for year-around four or six inch pot production and distinguished by its profuse display of closely massed flowers which are of a light red color upon first opening and which quickly turn to a bright pink, giving the head of flowers a pleasing two-tone appearance. This plant has a vigorous and rapid growth habit and an abundant production of large leaves spreading outwardly below the large and bright clusters of flowers.

2 Drawing Figures

BACKGROUND OF THE NEW PLANT

This new variety of kalanchoe plant originated as a seedling of a variety resulting from breeding efforts carried on by me at Cartago, Costa Rica, with the object of developing new and distinct kalanchoe varieties for pot plant production.

The geneology of this new plant is as follows:

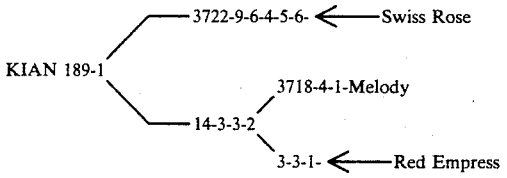

The seeds of KIAN 189-1 were collected in February of 1977 and sown in June of that year. This plant was selected by me in January 1978 and was first asexually propagated by me about three weeks later for observation and test. Subsequent propagation of this plant through successive generations by cuttings at Cartago, Costa Rica, has demonstrated that its novel characteristics hold true from generation to generation and appear to be firmly fixed. Propagation of this new variety is now being done at West Chicago, Ill., and at Parrish, Fla.

DESCRIPTION OF THE DRAWINGS

This new kalanchoe cultivar is illustrated by the accompanying drawings, of which sheet 1 is a full color photographic print showing the growth and flowering character of the plant in full bloom; and sheet 2 is a hand-painted print showing a close-up view of the flowers of this plant, the colors shown being true to specification.

DESCRIPTION OF THE NEW PLANT

The following is a detailed description of this new kalanchoe variety based upon observations of greenhouse grown plants at West Chicago, Ill., in the Fall of 1979, the color designations being according to The R.H.S. Colour Chart published by The Royal Horticultural Society of London, England.

THE PLANT

Origin: Seedling.

Parentage:

*Seed parent.*—Swiss Rose (unpatented).

*Pollen parent.*—An unnamed seedling of Melody (unpatented) × Red Empress (unpatented).

Classification:

*Botanic.*—*Kalanchoe blossfeldiana.*

*Commercial.*—Pot Kalanchoe.

Form: Bush.

Shape: Vase.

Height: Variable.

Growth: Vigorous, upright and strong.

Growth rate: Rapid.

Branching: Caespitose.

Foliage:

*Leaf size.*—About 25 to 40 mm. wide and about 35 to 55 mm. long.

*Shape.*—Ovate with cuneate base and crenate margins.

*Texture.*—Fleshy and smooth.

*Surface aspect.*—Glossy.

*Ribs and veins.*—Netted.

*Color.*—Upper side—147A. Under side—147C.

*Petioles.*—Length—variable, about 5 to 10 mm.

THE BUD

Shape: Long pointed.

Size: Normal but variable.

Opening rate: Normal.

Sepals: Four in number, hooded over the bud.

*Appearance.*—When flowers open, sepals are upstanding and awl shape.

*Color.*—Inside—137D. Outside—137D.

Calyx:

*Shape.*—Pear-shaped.

*Size.*—Small.

*Splitting.*—Calyx does split.

*Aspect.*—Smooth.

Peduncle:

*Length.*—Variable.

*Strength.*—Rigid and erect.

*Aspect.*—Smooth.

*Color.*—137A-137D.

THE FLOWER

Recommended flowering: Year around with photoperiod control.

Response: 10 to 12 weeks.

Blooming habit: Intermittent and profusely.

Blooms:

*Size.*—Small. Diameter: about 10 mm. Depth: about 12 mm.

*Borne.*—In a panicle cluster.

*Shape.*—Cup-shaped when bloom first opens, becoming flat as the flower matures.

Petalage:

*Number of petals.*—Four.

*Arrangement.*—Sympetalous, imbricated and in funnel form.

*Shape.*—Generally oval with rounded apex and entire margin.

*Texture.*—Soft.

*Appearance.*—Satiny.

*Color.*—Upper side—40B changing to 57C. Reverse side—37C.

Persistence: Flowers hang on and dry.

Effect of weather: Very little.

Fragrance: None.

Lasting quality: 5 to 6 weeks on plant.

REPRODUCTIVE ORGANS

Stamens: Number—eight in didynamous arrangement.

*Anthers.*—Size: insignificant. Color: yellow.

*Filaments.*—Insignificant in length and color.

*Pollen.*—Color—yellow.

Pistils: Number—four.

*Styles.*—Length: insignificant. Color: green.

*Stigmas.*—Color—green turning white.

Ovaries: Four superior ovaries.

This kalanchoe cultivar can be flowered the year around under photoperiod control and has a substantially uniform ten to twelve week flowering response. This plant grows rapidly and flowers profusely with panicle clusters standing high above a bed of medium sized, glossy foliage. This plant is particularly distinguished by its flowers, which are of a light red color when first opening but quickly turn to a bright pink giving the head of flowers a pleasing two-tone appearance.

I claim:

1. A new and distinct kalanchoe cultivar, substantially as herein shown and described, characterized in particular by its massed profuse production of small flowers which are of a light red color upon first opening but soon turning to a bright pink.

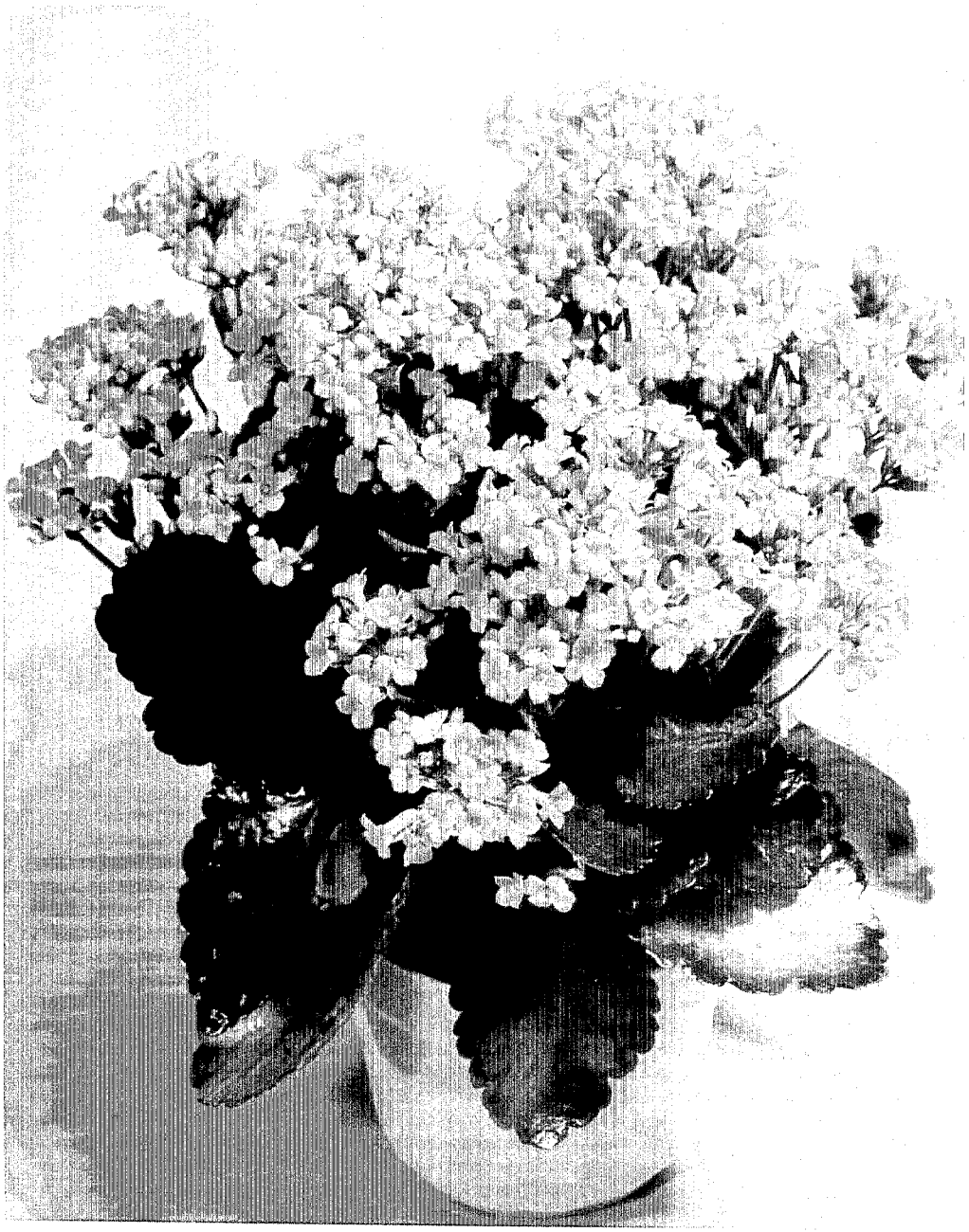

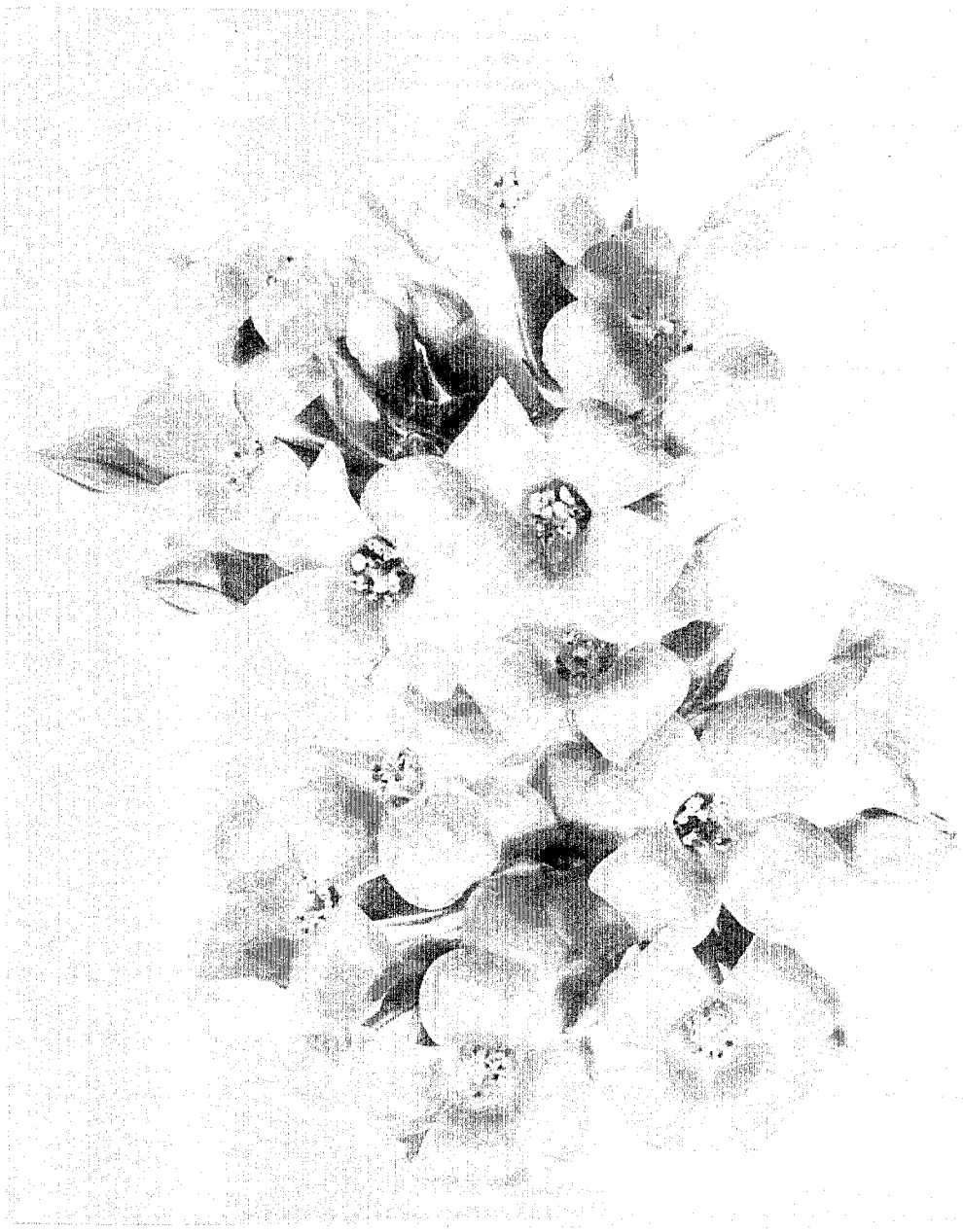

* * * * *